US012559416B2

(12) United States Patent
Zhang et al.

(10) Patent No.: US 12,559,416 B2
(45) Date of Patent: Feb. 24, 2026

(54) LITHIUM DISILICATE GLASS-CERAMIC WITH HIGH STRENGTH AND HIGH TRANSPARENCY AND PREPARATION METHOD AND USE THEREOF

(71) Applicant: AIDITE (QINHUANGDAO) TECHNOLOGY CO., LTD., Qinhuangdao (CN)

(72) Inventors: Jiaxin Zhang, Qinhuangdao (CN); Quanyi Nie, Qinhuangdao (CN); Lijia Zhao, Qinhuangdao (CN); Shenggang Zhou, Qinhuangdao (CN); Yong Yu, Qinhuangdao (CN); Xiaojun Wang, Qinhuangdao (CN)

(73) Assignee: AIDITE (QINHUANGDAO) TECHNOLOGY CO., LTD., HE (CN)

( * ) Notice: Subject to any disclaimer, the term of this patent is extended or adjusted under 35 U.S.C. 154(b) by 21 days.

(21) Appl. No.: 17/802,757

(22) PCT Filed: Jul. 8, 2022

(86) PCT No.: PCT/CN2022/104493
§ 371 (c)(1),
(2) Date: Aug. 26, 2022

(87) PCT Pub. No.: WO2023/011105
PCT Pub. Date: Feb. 9, 2023

(65) Prior Publication Data
US 2024/0199472 A1    Jun. 20, 2024

(30) Foreign Application Priority Data

Aug. 6, 2021    (CN) ........................ 202110901288.X

(51) Int. Cl.
*C03C 10/00*      (2006.01)
*A61K 6/833*      (2020.01)
(Continued)

(52) U.S. Cl.
CPC .............. *C03C 10/00* (2013.01); *A61K 6/833* (2020.01); *C03B 5/18* (2013.01); *C03B 19/02* (2013.01);
(Continued)

(58) Field of Classification Search
CPC ...... C03C 10/00; C03C 10/0027; A61K 6/833
See application file for complete search history.

(56) References Cited

U.S. PATENT DOCUMENTS 9,676,656 B2    6/2017  Kim et al.

FOREIGN PATENT DOCUMENTS

CN        104108883 A      10/2014
CN        107555798 A       1/2018
(Continued)

OTHER PUBLICATIONS

CN108467205A machine translation (Year: 2018).*

*Primary Examiner* — Cameron K Miller

(57) ABSTRACT

The present disclosure discloses a lithium disilicate glass-ceramic with high strength and high transparency and a preparation method and use thereof. A raw material composition of the lithium disilicate glass-ceramic comprises: 63-75 wt % of $SiO_2$, 13-18 wt % of $Li_2O$, 1-6 wt % of $Al_2O_3$, 1-10 wt % of $K_2O$, 2-6 wt % of $P_2O_5$, 0-4 wt % of an additive and 0-10 wt % of a colorant; a main crystal phase of the lithium disilicate glass-ceramic is lithium disilicate crystals, and an impurity phase of the lithium disilicate glass-ceramic is any one or a combination of at least two selected from the group consisting of lithium metasilicate, lithium phosphate and quartz; the lithium disilicate crystal has a size larger than 700 nm and a length-diameter ratio not less than 3.

19 Claims, 3 Drawing Sheets

(51) Int. Cl.

| | | |
|---|---|---|
| *C03B 5/18* | (2006.01) | |
| *C03B 19/02* | (2006.01) | |
| *C03B 25/02* | (2006.01) | |
| *C03B 32/02* | (2006.01) | |
| *C03C 4/00* | (2006.01) | |

(52) U.S. Cl.

CPC .............. *C03B 25/02* (2013.01); *C03B 32/02* (2013.01); *C03C 4/0021* (2013.01); *C03C 2204/00* (2013.01)

(56) References Cited

FOREIGN PATENT DOCUMENTS

| CN | 107698167 A | 2/2018 |
|----|-------------|--------|
| CN | 108069611 A | 5/2018 |
| CN | 108328932 A | 7/2018 |
| CN | 108423996 A | 8/2018 |
| CN | 108467205 A | 8/2018 |
| CN | 109824351 A | 5/2019 |
| CN | 113501668 A | 10/2021 |

* cited by examiner

LITHIUM DISILICATE GLASS-CERAMIC WITH HIGH STRENGTH AND HIGH TRANSPARENCY AND PREPARATION METHOD AND USE THEREOF

CROSS REFERENCE TO RELATED APPLICATION

This patent application claims the benefit and priority of Chinese Patent Application No. 202110901288.X, entitled "Lithium disilicate glass-ceramic with high strength and high transparency and preparation method and use thereof" filed on Aug. 6, 2021, the disclosure of which is incorporated by reference herein in its entirety as part of the present application.

TECHNICAL FIELD

The present disclosure belongs to the technical field of microcrystalline glasses, and specifically relates to a glass-ceramic and a preparation method and use thereof, in particular to a lithium disilicate glass-ceramic with high strength and high transparency and a preparation method and use thereof.

BACKGROUND ART

Lithium disilicate glass-ceramic is a microcrystalline glass having uniformly distributed crystal phase and glass phase and a compact structure. Due to the good optical matching between the refractive index ($1.55$) of a lithium disilicate crystal formed via crystallization and that ($1.50$) of a glass matrix, the lithium disilicate glass-ceramic has an excellent semi-light transparency, by which the color and light transparency of natural teeth may be simulated to the maximum extent, and thus has an excellent aesthetic effect. In addition, due to the good mechanical properties and the inherent property of the glass matrix being easily acid-etched with HF, the lithium disilicate glass-ceramic may solve the problems of occlusion and bonding during tooth repair quite well. Therefore, the lithium disilicate glass-ceramic has become a preferred material for anterior teeth aesthetic restoration.

Currently, the products clinically using lithium disilicate glass-ceramics for tooth repair mainly include the IPS series of Ivoclar-Vivadent and ZLS (zirconia-reinforced lithium silicate) series of Dentsply Sirona. However, since the three-point bending strength of these products is generally within a range of 360 to 440 Mpa, the products are very easy to be cracked or fractured due to the wearing of jaw teeth or the contact with hard food during actual occlusion, resulting in great hidden dangers and additional economic input for patients. Therefore, a lot of researches have been made to increase the strength and to improve the reliability and service life of lithium disilicate glass-ceramics.

For example, CN109824351A discloses a high-strength dental repair ceramic composite material, in which $ZrSiO_4$ is added to the glass-ceramic components and then is decomposed and generates $ZrO_2$ microcrystals in situ during heat treatment. The $ZrO_2$ microcrystals may undergo a phase transition from tetragonal phase to monoclinic phase during cooling to result in volume expansion, thus forming an extrusion effect on the surrounding lithium disilicate crystals. With the compressive stress as produced under the extrusion effect, the bending strength of the lithium disilicate glass-ceramics is increased to 420 to 479 MPa. U.S. Pat. No. 9,676,656B$_2$ discloses a high-strength and aesthetic lithium disilicate crystalline glass containing cristobalite crystals and a preparation method thereof, in which the glass-ceramic with lithium disilicate as a main crystal phase and quartz as a second phase is prepared by adding a high content of $SiO_2$. Utilizing the compressive stress that is easily produced due to a greater thermal expansion coefficient of quartz ($10.9 \times 10^{-6}/°$ C.) than that of a glass matrix during heat treatment, the bending strength of the glass-ceramic is increased to 380 to 440 MPa. CN104108883A discloses high-strength lithium disilicate glass-ceramics and a preparation method thereof, in which the glass-ceramic with lithium disilicate as a main crystal phase and magnesium aluminum silicate and beta-quartz as a impurity phase is prepared by adding a relatively high content of MgO and $Al_2O_3$ to the components, followed by a heat treatment to fully react MgO with $Al_2O_3$ and $SiO_2$. Under the inherent compressive stress, the strength of the glass-ceramic is increased to 705 MPa. Although the methods above improve the bending strength to a certain extent, the strength improvement is still limited. Moreover, the refractive index of the second phase (impurity phase) introduced does not match that of the glass matrix, which may cause the problem of reduced light transparency, such that the glass-ceramics can be used only for the pontic restoration at posterior teeth positions in practical application.

CN108069611A discloses a lithium silicate microcrystalline glass and lithium disilicate microcrystalline glass with high transparency and a preparation method and application thereof. In the method above, the crystal size of lithium disilicate is controlled to be less than 200 nm by adjusting the mass ratio of $SiO_2$ to $Li_2O$ in the components. Since the crystal size is smaller than the range of 380 to 780 nm for visible light, the glass-ceramics prepared show a relatively high light transparency. However, such a fine crystal size cannot afford a microstructure with good three-dimensional interweaving and crystal grain interlocking, and thus the strength still remains at the existing level of 360 to 450 MPa.

In addition, high fracture toughness is also one of the important indicators to evaluate the reliability and resistance to the risk of cracking or fracturing of glass-ceramics. The IPS series of Ivoclar Vivadent has a fracture toughness of 2.0 to 2.5 MPa·m$^{1/2}$. According to IS06872, if the fracture toughness is higher than 3.0 MPa·m$^{1/2}$, the product may be effectively used as a three-unit pontic for anterior teeth; if the fracture toughness is higher than 3.5 MPa·m$^{1/2}$, the product may be used as a three-unit pontic for posterior teeth. However, the fracture toughness of most glass-ceramics currently is difficult to meet this requirement.

Therefore, it is of great significance in the field of dental restoration to develop a lithium disilicate glass-ceramic with high strength, high transparency and high fracture toughness, which may effectively reduce the risk of chipping of restorations and simulate the toughness and light transparency of natural teeth well.

SUMMARY

In view of the problems existing in the prior art, an objective of the present disclosure is to provide a lithium disilicate glass-ceramic with high strength and high transparency and a preparation method and use thereof. According to the lithium disilicate glass-ceramic, by means of optimizing the composition and proportions and adjusting the reaction conditions during heat treatment, the lithium disilicate prepared are controllable in size of crystal grains, the three-point bending strength reaches a range of 450-750 MPa, and the optical transmittance of a sample with a thickness of 1 mm at 550 nm is adjustable within a range of 10%-80%. Therefore, the risk of chipping of restorations is effectively reduced and the toughness and light transparency of natural teeth are simulated well.

In order to achieve the objective above, the present disclosure provides the following technical solutions.

In the first aspect, the present disclosure provides a lithium disilicate glass-ceramic with high strength and high transparency, a raw material composition of the lithium disilicate glass-ceramic comprising: 63-75 wt % of $SiO_2$, such as 63 wt %, 65 wt %, 67 wt %, 69 wt %, 71 wt %, 73 wt % or 75 wt %; 13-18 wt % of $Li_2O$, such as 13 wt %, 14 wt %, 15 wt %, 16 wt %, 17 wt % or 18 wt %; 1-6 wt % of $Al_2O_3$, such as 1 wt %, 2 wt %, 3 wt %, 4 wt %, 5 wt % or 6 wt %; 1-10 wt % of $K_2O$, such as 1 wt %, 3 wt %, 5 wt %, 7 wt % or 10 wt %; 2-6 wt % of $P_2O_5$, such as 2 wt %, 3 wt %, 4 wt %, 5 wt % or 6 wt %; 0-4 wt % of an additive, such as 0 wt %, 1 wt %, 2 wt %, 3 wt % or 4 wt %; 0-10 wt % of a colorant, such as 0 wt %, 2 wt %, 4 wt %, 6 wt %, 8 wt % or 10 wt %. The selection of the numerical values above is not limited to the listed values, and other unlisted values within the respective numerical ranges are also applicable.

A main crystal phase of the lithium disilicate glass-ceramic is lithium disilicate crystals. An impurity phase of the lithium disilicate glass-ceramic is any one or a combination of at least two selected from the group consisting of lithium metasilicate, lithium phosphate and quartz, and the typical but non-restrictive examples of the combination comprise a combination of lithium metasilicate and lithium phosphate and a combination of lithium phosphate and quartz. The lithium disilicate crystal has a size larger than 700 nm, such as 710 nm, 800 nm, 900 nm, 1000 nm, 1100 nm, 1200 nm or 1300 nm, and a length-diameter ratio not less than 3, such as 3, 4, 5 or 6. The selection of the numerical values above is not limited to the listed values, and the other unlisted values within the respective numerical ranges are also applicable.

In the present disclosure, the size of the lithium disilicate crystal is larger than 700 nm, and the length-diameter ratio is not less than 3, in which the morphology of the lithium disilicate crystal is fusiform. The term "size of the lithium disilicate crystal" refers to the length of the long axis of the fusiform crystal. The term "length-diameter ratio" refers to the ratio of length to width.

In the present disclosure, the strength, fracture toughness and light transparency of the lithium disilicate glass-ceramic are improved by increasing the size of lithium disilicate crystals to make it close to or larger than the range of maximum wavelength of visible light (380 nm-780 nm). This is distinct from the prior art that a good light transparency can only be achieved with a crystal size smaller than the minimum wavelength of visible light. This is because when the size of crystals is larger, the amount of crystals in a given space is less. Correspondingly, the crystal boundaries between the glass matrix and the lithium disilicate crystals are decreased, and thus the scattering effect of the crystal boundaries on light is weakened, thereby improving the light transparency.

The followings are preferred technical solutions of the present disclosure, which are not deemed as limitations of the technical solutions provided in the present disclosure. The technical objectives and beneficial effects of the present disclosure may be better achieved and realized with the following technical solutions.

In the present disclosure, in some embodiments, the raw material composition of the lithium disilicate glass-ceramic comprises: 65-70 wt % of $SiO_2$, such as 65 wt %, 67 wt %, 69 wt % or 70 wt %; 14-16 wt % of $Li_2O$, such as 14 wt %, 15 wt % or 16 wt %; 2-5 wt % of $Al_2O_3$, such as 2 wt %, 3 wt %, 4 wt % or 5 wt %; 2-8 wt % of $K_2O$, such as 2 wt %, 3 wt %, 5 wt %, 7 wt % or 8 wt %; 3-5 Wt % of $P_2O_5$, such as 3 wt %, 4 wt % or 5 wt %; 1-3 wt % of an additive, such as 1 wt %, 2 wt % or 3 wt %; 2-5 wt % of a colorant, such as 2 wt %, 3 wt %, 4 wt % or 5 wt %. The selection of the numerical values above is not limited to the listed values, and other unlisted values within the respective numerical ranges are also applicable.

In some embodiments, the raw material composition of the lithium disilicate glass-ceramic further comprises: 0-6 wt % of CaO, such as 1 wt %, 2 wt %, 3 wt %, 4 wt %, 5 wt % or 6 wt %; 0-5 wt % of BaO, such as 1 wt %, 2 wt %, 3 wt %, 4 wt % or 5 wt %; 0-10 wt % of $B_2O_3$, such as 0.1 wt %, 2 wt %, 4 wt %, 6 wt %, 8 wt % or 10 wt %; 0-10 wt % of $ZrO_2$ or $HfO_2$, such as 0.1 wt %, 2 wt %, 4 wt %, 6 wt %, 8 wt % or 10 wt %. The typical but non-restrictive examples of the combination comprise a combination of CaO and BaO, a combination of CaO, BaO and $B_2O_3$, and a combination of BaO, $B_2O_3$ and $ZrO_2$.

In the present disclosure, in some embodiments, the additive comprises a monovalent metal oxide and a divalent metal oxide.

In some embodiments, the monovalent metal oxide comprises any one or a combination of at least two selected from the group consisting of $Na_2O$, $Rb_2O$ and $Cs_2O$, and the typical but non-restrictive examples of the combination comprise a combination of $Na_2O$ and $Rb_2O$, a combination of $Rb_2O$ and $Cs_2O$, and a combination of $Na_2O$, $Rb_2O$ and $Cs_2O$.

In some embodiments, the divalent metal oxide comprises any one or a combination of at least two selected from the group consisting of MgO, SrO and ZnO, and the typical but non-restrictive examples of the combination comprise a combination of MgO and SrO, a combination of SrO and ZnO, and a combination of MgO, SrO and ZnO.

In the present disclosure, in some embodiments, the colorant comprises any one or a combination of at least two selected from the group consisting of $Fe_2O_3$, $TiO_2$, $CeO_2$, CuO, $Cr_2O_3$, MnO, $SeO_2$, $V_2O_5$, $In_2O_3$ and a rare earth oxide. The typical but non-restrictive examples of the combination comprise a combination of $TiO_2$, $CeO_2$ and CuO, a combination of $Fe_2O_3$ and $TiO_2$, a combination of MnO, $SeO_2$, $V_2O_5$ and $In_2O_3$, and a combination of $V_2O_5$, $In_2O_3$ and a rare earth oxide.

In some embodiments, the rare earth oxide comprises any one or a combination of at least two selected from the group consisting of $La_2O_3$, $Nd_2O_3$, $Tb_2O_3$, $Pr_6O_{11}$ and $Er_2O_3$. The typical but non-restrictive examples of the combination comprise a combination of $La_2O_3$ and $Nd_2O_3$, a combination of $Nd_2O_3$, $Tb_2O_3$ and $Pr_6O_{11}$, and a combination of $Pr_6O_{11}$ and $Er_2O_3$.

In the present disclosure, in some embodiments, the lithium disilicate crystal is fusiform.

In some embodiments, the lithium disilicate crystal has a microstructure with three-dimensional interweaving and crystal grain interlocking.

In the present disclosure, in some embodiments, a light transmittance of a sample of the lithium disilicate glass-ceramic with a thickness of 1 mm at 550 nm is within a range of 10%-40%, such as 10%, 15%, 20%, 25%, 30%, 35% or 40%, provided that the lithium disilicate crystal has a size larger than 700 nm and smaller than 1200 nm and a length-diameter ratio within a range of 3-5. However, the numerical values are not limited to the listed values, and the other unlisted values within the respective numerical ranges are also applicable.

In some embodiments, a light transmittance of a sample of the lithium disilicate glass-ceramic with a thickness of 1 mm at 550 nm is within a range of 40%-80%, such as 40%, 45%, 50%, 55%, 60%, 65%, 70%, 75% or 80%, provided that the lithium disilicate crystal has a size not smaller than 1200 nm and a length-diameter ratio not less than 5. However, the numerical values are not limited to the listed values, and the other unlisted values within the respective numerical ranges are also applicable.

In the second aspect, the present disclosure provides a method for preparing the lithium disilicate glass-ceramic as described above, comprising:

(1) mixing raw materials of the lithium disilicate glass-ceramic in proportion, followed by melting to obtain a basic glass liquid; and (2) subjecting the basic glass liquid obtained in step (1) to a molding annealing treatment and a heat treatment in sequence to obtain the lithium disilicate glass-ceramic.

In the present disclosure, according to the preparation method, the raw materials are fully melted until the bubbles escape completely to ensure the uniformity of quality and color in the glass blocks that are obtained subsequently. Then a molding annealing treatment is performed to eliminate the internal stress of the substrate glass, which prevents cracking or chipping during processing caused by the excessive temperature difference and thus the accumulation of a large amount of internal stress inside. Thereafter, the nucleation-growth process of the crystal grains is adjusted and controlled through a heat treatment, so as to obtain lithium disilicate crystals with a size larger than 700 nm and a length-diameter ratio not less than 3. The relatively high length-diameter ratio enables lithium silicate crystals to form a microstructure with three-dimensional interweaving and crystal grain interlocking, thereby improving the three-point bending strength and fracture toughness of the glass-ceramics.

In the present disclosure, in some embodiments, in step (1), the mixing is performed on a mixer.

In some embodiments, in step (1), the mixing is performed for 30-300 min, such as 30 min, 60 min, 90 min, 120 min, 150 min, 180 min, 210 min, 240 min, 270 min or 300 min. However, the numerical values are not limited to the listed values, and the other unlisted values within the respective numerical ranges are also applicable.

In some embodiments, in step (1), the melting is performed at a temperature within a range of 1300-1600° C., such as 1300° C., 1350° C., 1400° C., 1450° C., 1500° C., 1550° C. or 1600° C. However, the numerical values are not limited to the listed values, and the other unlisted values within the respective numerical ranges are also applicable.

In some embodiments, in step (1), the melting is performed for 1-10 h, such as 1 h, 2 h, 3 h, 4 h, 5 h, 6 h, 7 h, 8 h, 9 h or 10 h. However, the numerical values are not limited to the listed values, and other unlisted values within the respective numerical ranges are also applicable.

In the present disclosure, in some embodiments, in step (2), the molding annealing treatment comprises: pouring the basic glass liquid into a mold for annealing to obtain a substrate glass.

In some embodiments, the mold is preheated to a temperature within a range of 200-500° C., such as 200° C., 300° C., 400° C. or 500° C. However, the numerical values are not limited to the listed values, and the other unlisted values within the respective numerical ranges are also applicable.

In some embodiments, the annealing is performed for 0.1-24 h, such as 0.1 h, 1 h, 5 h, 10 h, 15 h, 20 h or 24 h. However, the numerical values are not limited to the listed values, and the other unlisted values within the respective numerical ranges are also applicable.

In some embodiments, after the molding annealing treatment, the treated substrate glass is cooled to room temperature.

In some embodiments, the heat treatment comprises at least a first heat treatment and a last heat treatment.

In some embodiments, the heat treatment further comprises an intermediate heat treatment.

In the present disclosure, if the number of times of the heat treatment is 3, it is performed in the order of "first", "intermediate" and "last".

In some embodiments, the first heat treatment is performed at a temperature within a range of 500-600° C., such as 500° C., 520° C., 540° C., 560° C., 580° C. or 600° C. However, the numerical values are not limited to the listed values, and the other unlisted values within the respective numerical ranges are also applicable.

In some embodiments, the first heat treatment is performed for 60-240 min, such as 60 min, 90 min, 120 min, 150 min, 180 min, 210 min or 240 min. However, the numerical values are not limited to the listed values, and the other unlisted values within the respective numerical ranges are also applicable.

In some embodiments, the intermediate heat treatment is performed at a temperature within a range of 600-700° C., such as 600° C., 620° C., 640° C., 660° C., 680° C. or 700° C. However, the numerical values are not limited to the listed values, and the other unlisted values within the respective numerical ranges are also applicable.

In some embodiments, the intermediate heat treatment is performed for 30-240 min, such as 30 min, 60 min, 90 min, 120 min, 150 min, 180 min, 210 min or 240 min. However, the numerical numbers are not limited to the listed values, and the other unlisted values within the respective numerical ranges are also applicable.

In some embodiments, the last heat treatment is performed at a temperature within a range of 800-860° C., such as 800° C., 810° C., 820° C., 830° C., 840° C., 850° C. or 860° C. However, the numerical values are not limited to the listed values, and the other unlisted values within the respective numerical ranges are also applicable.

In some embodiments, the last heat treatment is performed for 1-30 min, such as 1 min, 5 min, 10 min, 15 min, 20 min, 25 min or 30 min. However, the numerical values are not limited to the listed values, and the other unlisted values within the respective numerical ranges are also applicable.

In the present disclosure, the first heat treatment to the substrate glass may form a large amount of crystal nuclei in the glass matrix; the intermediate heat treatment enables formation of a glass-ceramic with lithium metasilicate as a main crystal phase; the last heat treatment enables formation of a glass-ceramic with lithium disilicate as a main crystal phase. Accordingly, the temperature and time for each heat treatment are very important. If the temperature for the first heat treatment is excessively low, it will be difficult to nucleate in the glass matrix or the amount of nucleation is small, and thus the uniform growth of the lithium metasilicate crystals during the intermediate heat treatment cannot be effectively controlled. If the temperature for the first heat

7 | 8 treatment is excessively high, a large amount of crystal nuclei would grow up to form the lithium metasilicate crystals, which is not conducive to controlling the size of lithium disilicate crystals. If the temperature for the intermediate heat treatment is excessively low, it would be difficult to ensure a sufficient amount of crystal nuclei to grow up to form lithium metasilicate crystals that are easy for processing, resulting in the deterioration in processability. If the temperature for the intermediate heat treatment is excessively high, the lithium metasilicate crystals are prone to be converted into lithium disilicate crystals that are difficult for processing, leading to a decrease in processability. If the temperature for the last heat treatment is excessively low, it would be very difficult to form lithium disilicate crystals with a relatively high length-diameter ratio, resulting in low strength. If the temperature for the last heat treatment is excessively high, an abnormal growth of lithium disilicate crystals would be caused, leading to decrease in strength and light transparency.

In some embodiments, the substrate glass or an intermediate product before the last heat treatment is subjected to CAD/CAM machining to be formed into the shape of a tooth to be repaired.

In some embodiments, the substrate glass or an intermediate product before the last heat treatment is formed into the shape of a tooth to be repaired by a hot pressing process or a lost wax process.

In the present disclosure, in some embodiments, the preparation method comprises the following steps:

(1) placing raw materials of a lithium disilicate glass-ceramic into a mixer in proportion, mixing for 30-300 min, and then melting at a temperature within a range of 1300-1600° C. for 1-10 h to obtain a basic glass liquid after the components are uniformly distributed and the bubbles escape completely;

(2) pouring the basic glass liquid obtained in step (1) into a mold at a temperature within a range of 200-500° C. for annealing for 0.1-24 h, and then naturally cooling to room temperature to obtain a substrate glass; and heating the substrate glass to a temperature within a range of 500-600° C. and holding for 60-240 min, and then heating to a temperature within a range of 600-700° C. and holding for 30-240 min; processing the obtained intermediate product into the shape of a tooth to be repaired by CAD/CAM machining, the hot pressing process or the lost wax process, and then grinding and polishing the surface; finally, placing the processed sample in a high-temperature electric furnace, and holding at a temperature in a range of 800-860° C. for 1-30 min to obtain a lithium disilicate glass-ceramic with lithium disilicate crystals as the main crystal phase.

In the third aspect, the present disclosure provides use of the lithium disilicate glass-ceramic as described above, where the lithium disilicate glass-ceramic is used for making an oral restoration.

In some embodiments, the oral restoration comprises any one of dental veneers, inlays, onlays, abutment teeth, single crowns, anterior multi-unit pontic and posterior multi-unit pontic.

Compared with the prior art, the present disclosure has the following beneficial effects:

(1) In the lithium disilicate glass-ceramic according to the present disclosure, by means of increasing the size of the lithium disilicate crystals, a microstructure with three-dimensional interweaving and crystal grain interlocking may be well formed on the one hand, such that the lithium disilicate glass-ceramic has a three-point bending strength maintained between 450 and 750 MPa and a fracture toughness higher than 3.5 MPa·m$^{1/2}$; the increase in size of the crystals may weaken the scattering effect of the grain boundaries on light on the other hand, such that the light transmittance of a sample with a thickness of 1 mm at 550 nm is adjustable within a range of 10%-80%. The lithium disilicate glass-ceramic truly combines the excellent properties of high strength, high transparency and high fracture toughness, effectively reducing the risk of chipping and simulating the toughness and light transparency of natural teeth well.

(2) In the preparation method of the present disclosure, the size of crystals is adjusted by optimizing the formulation composition and controlling the conditions during the heat treatment.

The preparation method has a simple technological process, high economic benefit and desirable industrial application prospect.

DETAILED DESCRIPTION OF THE EMBODIMENTS

In order to better illustrate the present disclosure and to facilitate understanding of the technical solutions of the present disclosure, the present disclosure will be further described in detail below. However, the following embodiments are merely simple examples of the present disclosure without representing or limiting the protection scope of the present disclosure, and the protection scope of the present disclosure is subject to the claims.

The typical but non-restrictive examples of the present disclosure are as follows.

The raw material compositions of lithium disilicate glass-ceramics prepared according to the following examples and comparative example are shown in Table 1, in which the content of each component is represented as mass percentage.

TABLE 1

| Raw material proportions in Examples 1-6 | | | | | |
| --- | --- | --- | --- | --- | --- |
| | Example 1 | Example 2 | Example 3 | Example 4 | Example 5 | Example 6 |
| $SiO_2$ | 67.5 | 69 | 70 | 64.5 | 72 | 70 |
| $Li_2O$ | 14.7 | 16.7 | 13.4 | 15.5 | 13 | 14 |
| $K_2O$ | 4.2 | 3.2 | 6.1 | 5.7 | 3 | 3.4 |
| $Al_2O_3$ | 3.7 | 3.3 | 4.8 | 5.0 | 4 | 3.5 |
| $P_2O_5$ | 3.3 | 4.2 | 2.9 | 4.4 | 5 | 4.8 |
| $Rb_2O$ | 0.3 | 0.6 | 0.5 | 1.2 | 0.8 | 1.0 |
| $MgO$ | 1.0 | 0.4 | 0.6 | 0.5 | — | — |
| $CaO$ | 0.4 | — | 0.3 | — | — | 0.2 |
| $Fe_2O_3$ | 1.75 | 1.2 | 0.4 | 0.8 | 1.6 | 1.2 |
| $Tb_2O_3$ | 2.7 | 0.3 | 0.8 | 1.0 | 0.4 | 1.9 |
| $La_2O_3$ | 0.45 | 0.3 | 0.2 | 0.4 | 0.2 | — |
| $ZnO_2$ | — | 0.8 | — | 1.0 | — | — |

Example 1

This example provided a method for preparing a lithium disilicate glass-ceramic with high strength and high transparency, and the preparation method was performed by the following steps:

(1) Raw materials of a lithium disilicate glass-ceramic were placed into a mixer in proportion, mixed for 40 min, then placed in a platinum crucible and melted at 1450° C. for 5 h; after the components were evenly distributed and the bubbles escaped completely, a basic glass liquid was obtained.

(2) The basic glass liquid obtained in step (1) was poured into a mold at 420° C. for annealing for 10 h, and then naturally cooled to room temperature, obtaining a substrate glass.

The substrate glass was heated to 520° C., held for 130 min and naturally cooled to room temperature, followed by being heated to 660° C., held for 150 min and naturally cooled to room temperature; subsequently, the obtained intermediate product was processed into the shape of the tooth to be repaired by CAD/CAM machining, and then the surface was ground and polished; finally, the processed sample was placed in a high-temperature electric furnace and held at 840° C. for 2 min, obtaining a lithium disilicate glass-ceramic with $Li_2Si_2O_5$ crystals as the main crystal phase and $Li_2SiO_3$ and $Li_3PO_4$ as the impurity phase.

Figure 1:
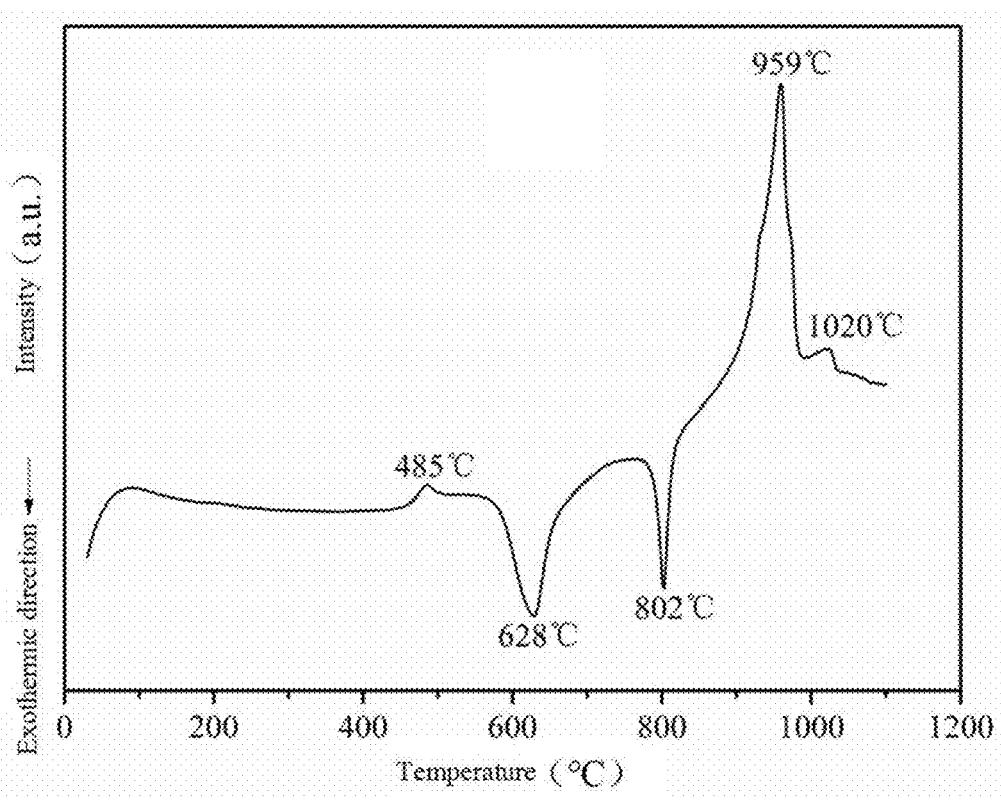
FIG. 1 shows a Differential Scanning Calorimetry (DSC) diagram of the lithium disilicate glass-ceramic provided in Example 1 of the present disclosure.
Figure 2:
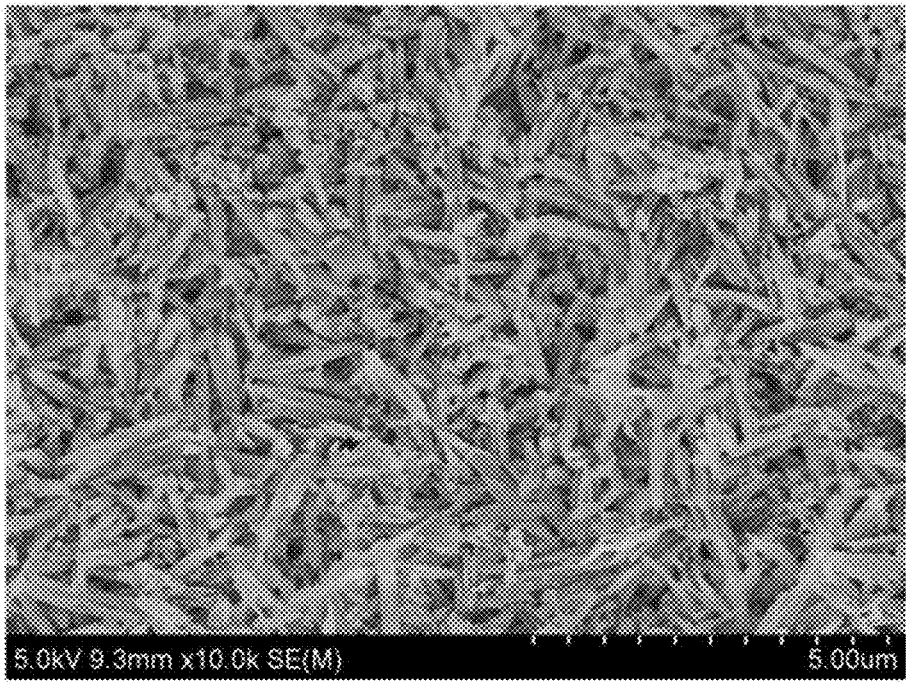
FIG. 2 shows a micro-morphology image of the lithium disilicate glass-ceramic provided in Example 1 of the present disclosure.
Figure 3:
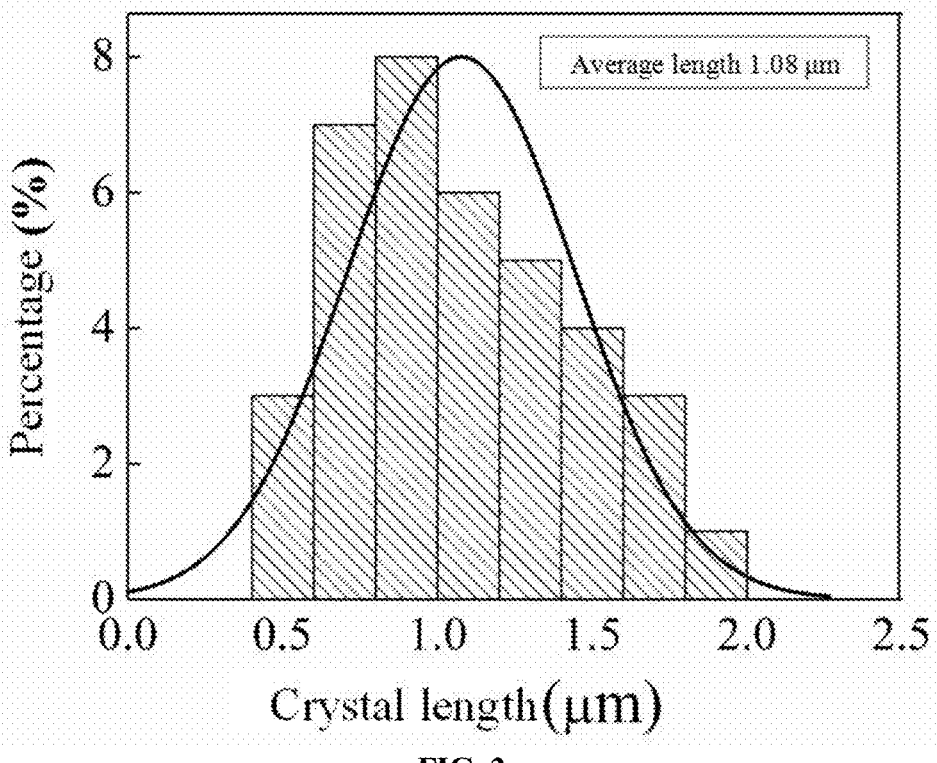
FIG. 3 shows a length size distribution diagram of the lithium disilicate crystals in the lithium disilicate glass-ceramic provided in Example 1 of the present disclosure.
Figure 4:
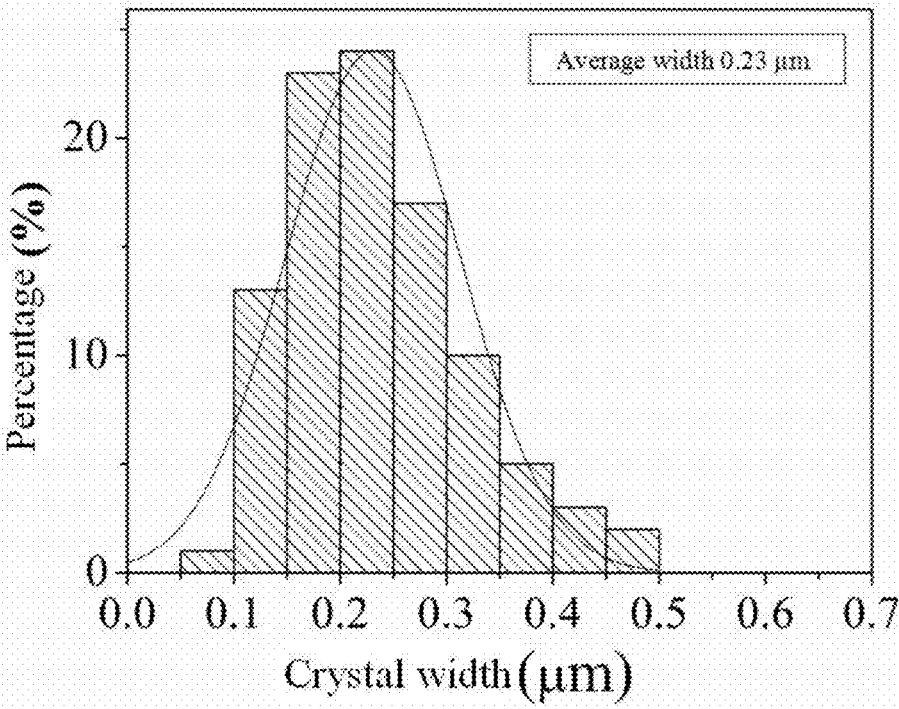
FIG. 4 shows a width size distribution diagram of the lithium disilicate crystals in the lithium disilicate glass-ceramic provided in Example 1 of the present disclosure.
Figures 5, 6:
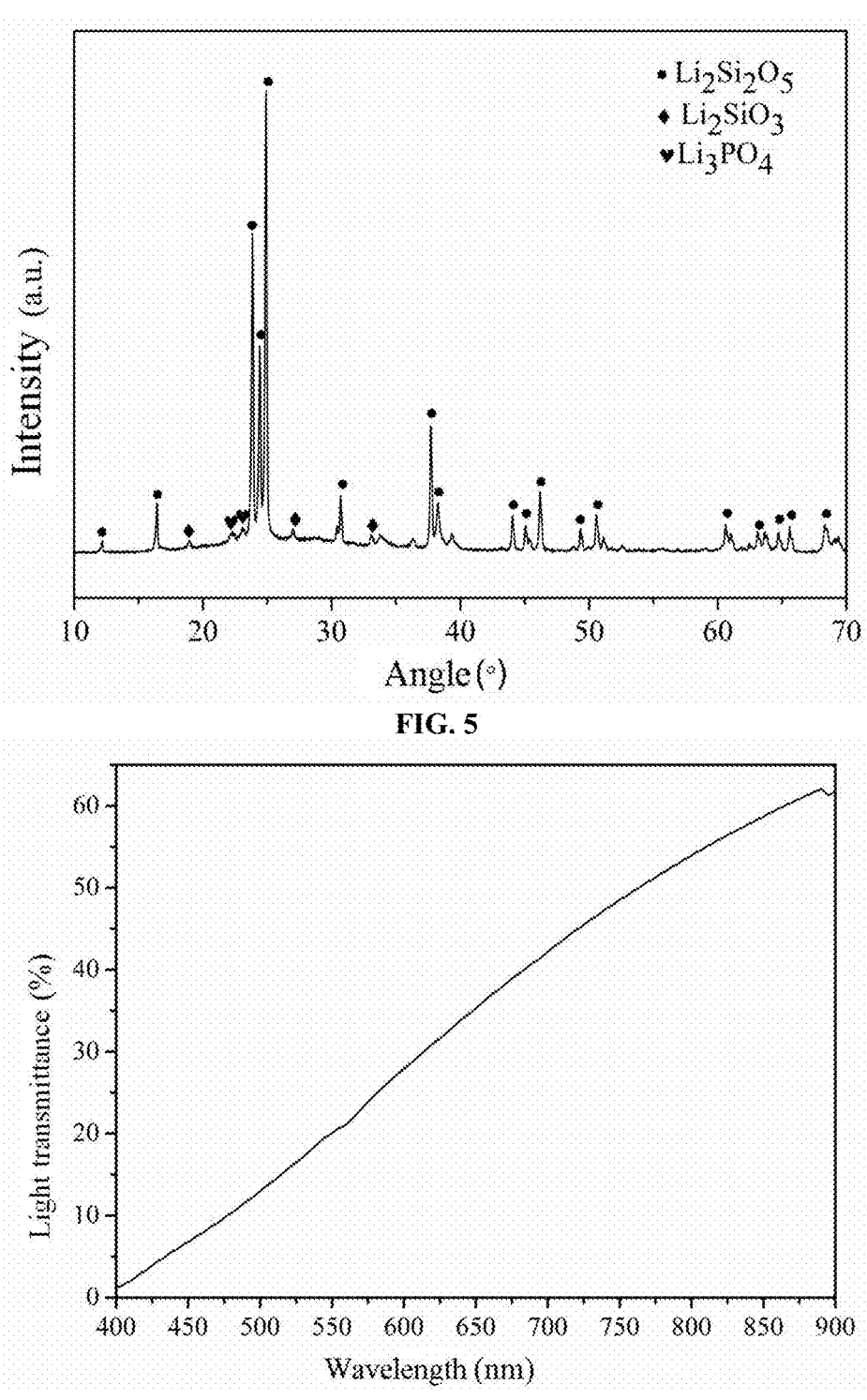
FIG. 5 shows an X-ray diffraction pattern (XRD) of the lithium disilicate glass-ceramic provided in Example 1 of the present disclosure.
FIG. 6 shows a light transmittance curve diagram of the lithium disilicate glass-ceramic provided in Example 1 of the present disclosure for visible light within a range of 400-900 nm.

The lithium disilicate glass-ceramic obtained as described above was characterized. The DSC diagram is shown in FIG. 1. The micro-morphology image is shown in FIG. 2. The length size distribution diagram of the lithium disilicate crystals is shown in FIG. 3. The width size distribution diagram of the lithium disilicate crystals is shown in FIG. 4. The XRD diagram of the lithium disilicate glass-ceramic is shown in FIG. 5. The light transmittance curve diagram of the lithium disilicate glass-ceramic for visible light within a range of 400 nm to 900 nm is shown in FIG. 6.

It may be seen from FIG. 1 that the glass transition temperature Tg of the sample is 485° C., which means that the formation of a large amount of crystal nuclei in the glass matrix is promoted effectively only at a heat treatment temperature higher than 485° C. 628° C. corresponds to the exothermic peak at which lithium metasilicate crystals are formed. 802° C. corresponds to the exothermic peak at which lithium disilicate crystals are formed. 959° C. corresponds to the softening point of the glass-ceramic, which indicates that the sample is prone to softening and deformation at a temperature higher than this.

It may be seen from FIG. 2 that the micro-morphology of the sample is fusiform and is distributed in the mechanism of three-dimensional interweaving and crystal grain interlocking. It may be further known from Table 3 that the fusiform lithium disilicate has a crystal size of 1080 nm and a length-diameter ratio of 4.7. A relatively high length-diameter ratio is conducive to the interweaving among the crystal grains, by which the three-point bending strength of the glass-ceramic is effectively improved to 580 MPa. In addition, the fracture mode of lithium disilicate glass-ceramics is intergranular fracture, and a relatively high length-diameter ratio can extend the path of crack propagation effectively, thereby dissipating the driving force of crack propagation and effectively improving the fracture toughness of the lithium disilicate glass-ceramic to 3.62 MPa·m$^{1/2}$, which meets the requirements of the international standard IS06872 for using as a three-unit pontic for posterior teeth.

It may be seen from FIG. 3 and FIG. 4 that the lithium disilicate crystals have an average length of 1.08 m and an average width of 0.23 m.

It may be seen from FIG. 5 that the main crystal phase of the sample is lithium disilicate ($Li_2Si_2O_5$) and impurity phases are lithium metasilicate ($Li_2SiO_3$) and lithium phosphate ($Li_3PO_4$).

It may be seen from FIG. 6 that the optical transmittance of the lithium disilicate glass-ceramic sample with a thickness of 1 mm at 550 nm is 20.11%, well meeting the requirements for a high light transmittance of dental restoration materials clinically (a sample with a thickness of 1 mm has an optical transmittance of 20-55% at a wavelength of 550 nm).

Example 2

This example provided a method for preparing a lithium disilicate glass-ceramic with high strength and high transparency, and the preparation method was performed by the following steps:

(1) Raw materials of a lithium disilicate glass-ceramic were placed into a mixer in proportion, mixed for 30 min, then placed in a platinum crucible and melted at 1450° C. for 3 h; after the components were evenly distributed and the bubbles escaped completely, a basic glass liquid was obtained.

(2) The basic glass liquid obtained in step (1) was poured into a mold at 400° C. for annealing for 3 h, and then naturally cooled to room temperature, obtaining a substrate glass.

The substrate glass was heated to 550° C., held for 100 min and naturally cooled to room temperature, followed by being heated to 660° C., held for 180 min and naturally cooled to room temperature; subsequently, the obtained intermediate product was processed into the shape of the tooth to be repaired by CAD/CAM machining, and then the surface was ground and polished; finally, the processed sample was placed in a high-temperature electric furnace and held at 840° C. for 6 min, obtaining a lithium disilicate glass-ceramic with $Li_2Si_2O_5$ crystals as the main crystal phase and $Li_2SiO_3$ as the impurity phase.

Example 3

This example provided a method for preparing a lithium disilicate glass-ceramic with high strength and high transparency, and the preparation method was performed by the following steps:

(1) Raw materials of a lithium disilicate glass-ceramic were placed into a mixer in proportion, mixed for 60 min, then placed in a platinum crucible and melted at 1450° C. for 5 h; after the components were evenly distributed and the bubbles escaped completely, a basic glass liquid was obtained.

(2) The basic glass liquid obtained in step (1) was poured into a mold at 450° C. for annealing for 2 h, and then naturally cooled to room temperature, obtaining a substrate glass.

The substrate glass was heated to 570° C., held for 140 min and naturally cooled to room temperature, followed by being heated to 670° C., held for 210 min and naturally cooled to room temperature; subsequently, the obtained intermediate product was processed into the shape of the tooth to be repaired by CAD/CAM machining, and then the surface was ground and polished; finally, the processed sample was placed in a high-temperature electric furnace and held at 830° C. for 10 min, obtaining a lithium disilicate glass-ceramic with $Li_2Si_2O_5$ crystals as the main crystal phase and $Li_2SiO_3$ as the impurity phase.

Example 4

This example provided a method for preparing a lithium disilicate glass-ceramic with high strength and high transparency, and the preparation method was performed by the following steps:

(1) Raw materials of a lithium disilicate glass-ceramic were placed into a mixer in proportion, mixed for 100 min, then placed in a platinum crucible and melted at 1600° C. for 3 h; after the components were evenly distributed and the bubbles escaped completely, a basic glass liquid was obtained.

(2) The basic glass liquid obtained in step (1) was poured into a mold at 450° C. for annealing for 4 h, and then naturally cooled to room temperature, obtaining a substrate glass.

The substrate glass was heated to 530° C., held for 120 min and naturally cooled to room temperature, followed by being heated to 630° C., held for 130 min and naturally cooled to room temperature; subsequently, the obtained intermediate product was processed into the shape of the tooth to be repaired by CAD/CAM machining, and then the surface was ground and polished; finally, the processed sample was placed in a high-temperature electric furnace and held at 860° C. for 3 min, obtaining a lithium disilicate glass-ceramic with $Li_2Si_2O_5$ crystals as the main crystal phase and $Li_2SiO_3$ and $Li_3PO_4$ as the impurity phase.

Example 5

This example provided a method for preparing a lithium disilicate glass-ceramic with high strength and high transparency, and the preparation method was performed by the following steps:

(1) Raw materials of a lithium disilicate glass-ceramic were placed into a mixer in proportion, mixed for 300 min, then placed in a platinum crucible and melted at 1300° C. for 10 h; after the components were evenly distributed and the bubbles escaped completely, a basic glass liquid was obtained.

(2) The basic glass liquid obtained in step (1) was poured into a mold at 200° C. for annealing for 24 h, and then naturally cooled to room temperature, obtaining a substrate glass.

The substrate glass was heated to 600° C., held for 60 min and naturally cooled to room temperature, followed by being heated to 700° C., held for 30 min and naturally cooled to room temperature; subsequently, the obtained intermediate product was processed into the shape of the tooth to be repaired by CAD/CAM machining, and then the surface was ground and polished; finally, the processed sample was placed in a high-temperature electric furnace and held at 850° C. for 1 min, obtaining a lithium disilicate glass-ceramic with $Li_2Si_2O_5$ crystals as the main crystal phase and $Li_2SiO_3$ as the impurity phase.

Example 6

This example provided a method for preparing a lithium disilicate glass-ceramic with high strength and high transparency, and the preparation method was performed by the following steps:

(1) Raw materials of a lithium disilicate glass-ceramic were placed into a mixer in proportion, mixed for 200 min, then placed in a platinum crucible and melted at 1500° C. for 1 h; after the components were evenly distributed and the bubbles escaped completely, a basic glass liquid was obtained.

(2) The basic glass liquid obtained in step (1) was poured into a mold at 500° C. for annealing for 0.1 h, and then naturally cooled to room temperature, obtaining a substrate glass.

The substrate glass was heated to 500° C., held for 240 min and naturally cooled to room temperature, followed by being heated to 600° C., held for 240 min and naturally cooled to room temperature; subsequently, the obtained intermediate product was processed into the shape of the tooth to be repaired by CAD/CAM machining, and then the surface was ground and polished; finally, the processed sample was placed in a high-temperature electric furnace and held at 800° C. for 30 min, obtaining a lithium disilicate glass-ceramic with $Li_2Si_2O_5$ crystals as the main crystal phase and $Li_2SiO_3$ and $Li_3PO_4$ as the impurity phase.

Example 7

This example provided a method for preparing a lithium disilicate glass-ceramic with high strength and high transparency, and the preparation method was performed by the following steps:

(1) Raw materials of a lithium disilicate glass-ceramic were placed into a mixer in proportion, mixed for 100 min, then placed in a platinum crucible and melted at 1400° C. for 4 h; after the components were evenly distributed and the bubbles escaped completely, a basic glass liquid was obtained.

(2) The basic glass liquid obtained in step (1) was poured into a mold at 450° C. for annealing for 5 h, and then naturally cooled to room temperature, obtaining a substrate glass.

The substrate glass was heated to 550° C., held for 240 min and naturally cooled to room temperature, subsequently, the obtained intermediate product was processed into the shape of the tooth to be repaired by CAD/CAM machining, and then the surface was ground and polished; finally, the processed sample was placed in a high-temperature electric furnace and held at 800° C. for 30 min, obtaining a lithium disilicate glass-ceramic with $Li_2Si_2O_5$ crystals as the main crystal phase and $Li_2SiO_3$ and $Li_3PO_4$ as the impurity phase.

Example 8

This example provided a method for preparing a lithium disilicate glass-ceramic with high strength and high transparency. The raw materials used were the same as those in Example 1. The preparation method referred to that in Example 1, with the only difference in that: in step (2), the first heat treatment of the substrate glass was performed at 450° C.

Example 9

This example provided a method for preparing a lithium disilicate glass-ceramic with high strength and high transparency. The raw materials used were the same as those in Example 3. The preparation method referred to that in Example 3, with the only difference in that: in step (2), the first heat treatment of the substrate glass was performed at 630° C.

Comparative Example 1

This comparative example provided a method for preparing a lithium disilicate glass-ceramic with high strength and high transparency. The raw materials used were the same as those in Example 1. The preparation method referred to that in Example 1, with the differences in that: in step (2), the substrate glass was heated to 670° C., held for 180 min and naturally cooled to room temperature; subsequently, the obtained intermediate product was processed into the shape of the tooth to be repaired by CAD/CAM machining, and then the surface was ground and polished; finally, the processed sample was placed in a high-temperature electric furnace and held at 840° C. for 5 min, obtaining a lithium disilicate glass-ceramic with $Li_2Si_2O_5$ crystals as the main crystal phase and $Li_2SiO_3$ as the impurity phase.

Firstly, the substrate glasses and intermediate products during heat treatments obtained in the preparation processes of Examples 1-9 and Comparative Example 1 were subjected to the corresponding phase analysis, and the results are shown in Table 2.

In Table 2 above, $T_g$ represents the glass transition temperature; $T_N$ and $t_N$ represent the temperature and time for the first heat treatment, respectively; $T_{P1}$ and $t_{P1}$ represent the temperature and time for the intermediate heat treatment, respectively; $T_{P2}$ and $t_{P2}$ represent the temperature and time for the last heat treatment, respectively.

Secondly, the crystal size, the length-diameter ratio, the light transmittance at 550 nm, the three-point bending strength, the hardness, the fracture toughness and the chemical solubility of the lithium disilicate glass-ceramics as prepared according to Examples 1-9 and Comparative Example 1 were measured. The test methods and conditions were as follows, and the test results are shown in Table 3.

① The crystal size was measured and counted using Nano Measurer 1.2 software.

② Light transmittance: the test sample was tested within a wavelength range of 400-900 nm using a spectrophotometer, and had a thickness of 1 mm.

③ Mechanical properties: the three-point bending strength and fracture toughness in the present disclosure were both characterized according to the ISO6872: 2008 international standard; for the test of three-point bending strength, 15 samples were tested and the average value of the obtained three-point bending strength values was calculated; for the test of fracture toughness, 10 samples were tested by the V notched beam (SEVNB) method to obtain the average value of the fracture toughness of the samples.

The hardness test in the present disclosure was in accordance with the ISO14705:2008 international standard; a Vickers hardness tester was used and a load of 1 kilogram-force (1 kgf) was applied; the test was performed for 15 times to obtain the average value of Vickers hardness of the samples.

④ Chemical solubility: the chemical solubility in the present disclosure was tested and analyzed according to the ISO6872:2008 international standard.

TABLE 2

Phase analysis of products of Examples 1-9 and Comparative Example 1

| | $T_g$ (° C.) | $T_N$ (° C.) | $t_N$ (min) | $T_{P1}$ (° C.) | $t_{P1}$ (min) | Crystal phase after $T_{P1}$ treatment | $T_{P2}$ (° C.) | $t_{P2}$ (min) | Crystal phase after $T_{P2}$ treatment | Processibility |
|---|---|---|---|---|---|---|---|---|---|---|
| Example 1 | 485 | 520 | 130 | 660 | 150 | $Li_2SiO_3$ | 840 | 2 | $Li_2Si_2O_5$ $Li_2SiO_3$ $Li_3PO_4$ | Very good |
| Example 2 | 480 | 550 | 100 | 660 | 180 | $Li_2SiO_3$ $Li_2Si_2O_5$ | 840 | 6 | $Li_2Si_2O_5$ $Li_2SiO_3$ | Good |
| Example 3 | 478 | 570 | 140 | 670 | 210 | $Li_2SiO_3$ $Li_2Si_2O_5$ | 830 | 10 | $Li_2Si_2O_5$ $Li_2SiO_3$ | Good |
| Example 4 | 489 | 530 | 120 | 630 | 130 | $Li_2SiO_3$ | 860 | 3 | $Li_2Si_2O_5$ $Li_2SiO_3$ $Li_3PO_4$ | Very good |
| Example 5 | 482 | 600 | 60 | 700 | 30 | $Li_2SiO_3$ $Li_2Si_2O_5$ | 850 | 1 | $Li_2Si_2O_3$ $Li_2SiO_3$ | Good |
| Example 6 | 472 | 500 | 240 | 600 | 240 | $Li_2SiO_3$ | 800 | 30 | $Li_2Si_2O_5$ $Li_2SiO_3$ $Li_3PO_4$ | Good |
| Example 7 | 486 | 550 | 240 | — | — | $Li_2SiO_3$ | 810 | 30 | $Li_2Si_2O_5$ $Li_2SiO_3$ | Good |
| Example 8 | 485 | 450 | 130 | 660 | 150 | $Li_2SiO_3$ | 840 | 2 | $Li_2Si_2O_5$ $Li_2SiO_3$ $Li_3PO_4$ | Very good |
| Example 9 | 478 | 630 | 140 | 670 | 210 | $Li_2SiO_3$ $Li_2Si_2O_5$ | 830 | 10 | $Li_2Si_2O_5$ $Li_2SiO_3$ | Good |
| Comparative Example 1 | 486 | — | — | 670 | 180 | $Li_2SiO_3$ $Li_2Si_2O_5$ | 840 | 5 | $Li_2Si_2O_5$ $Li_2SiO_3$ | Ordinary |

TABLE 3

Performance data of lithium disilicate glass-ceramics prepared in Examples 1-9
and Comparative Example 1

| | Crystal size (nm) | Length-diameter ratio | Light transmittance (at 550 nm) | Three-point bending strength (MPa) | Hardness (GPa) | Fracture toughness (MPa · m^{1/2}) | Chemical solubility (μg/cm^2) |
|---|---|---|---|---|---|---|---|
| Example 1 | 1080 | 4.7 | 20.11 | 580 | 5.76 | 3.62 | 34.4 |
| Example 2 | 1434 | 7.1 | 53.08 | 750 | 5.9 | 5.56 | 43.6 |
| Example 3 | 1110 | 4.8 | 21.28 | 595 | 6.2 | 3.58 | 41.3 |
| Example 4 | 1120 | 5.3 | 45.3 | 630 | 5.65 | 4.32 | 29.3 |
| Example 5 | 960 | 3.7 | 24.5 | 530 | 6.02 | 3.60 | 40.5 |
| Example 6 | 1200 | 4.2 | 28.7 | 580 | 6.32 | 3.77 | 38.8 |
| Example 7 | 920 | 4.0 | 26.5 | 560 | 5.85 | 4.02 | 44.0 |
| Example 8 | 750 | 3.2 | 12 | 470 | 6.60 | 3.52 | 44.5 |
| Example 9 | 800 | 3.8 | 17 | 488 | 6.45 | 3.60 | 42.2 |
| Comparative Example 1 | 960 | 2.6 | 10 | 380 | 6.70 | 2.37 | 45.2 |

Examples 1-6 are in accordance with the preparation method of the present disclosure. By means of optimizing the raw material components and adjusting the conditions of each heat treatment, the lithium disilicate glass-ceramic obtained has a light transmittance of 20.11-53.08% at a wavelength of 550 nm. This has fully met the requirements for high light transmittance of dental restoration materials in clinic, since the light transmittance of dental restoration materials is generally required to be maintained between 20-55% (at a wavelength of 550 nm) in clinic. Moreover, the lithium disilicate glass-ceramic obtained has good process-ability, and may reduce significantly the problems of such as chipping and the great wearing on machine needles during machining. In addition, since the lithium disilicate crystals have a size larger than 1080 nm and a length-diameter ratio more than 4.7, they may well form a microstructure with three-dimensional interweaving and crystal grain interlock-ing, such that the three-point bending strength of glass-ceramics is maintained at 580-750 MPa, effectively reducing the risk of chipping of the teeth. Furthermore, the lithium disilicate glass-ceramic obtained has a fracture toughness of 3.58-5.56 MPa·m^{1/2}, a hardness of 5.65-6.32 GPa and a chemical solubility of 29.3-43.6 μg/cm^2, which meet the requirements for dental materials clinically.

Example 7 is in accordance with the preparation method of the present disclosure. The lithium disilicate glass-ce-ramic obtained, although undergoing only two heat treat-ments, can still have a light transmittance of up to 26.5% at a wavelength of 550 nm and good processability. Mean-while, the three-point bending strength reaches 560 MPa, the fracture toughness reaches 4.02 MPa·m^{1/2}, the hardness reaches 5.85 GPa, and the chemical solubility is 44.0 μg/cm^2, which meet the requirements for dental materials clinically.

In contrast, in Example 8, the temperature for the first heat treatment is decreased during preparation, and the uniform growth of crystals during the heat treatment processes could not be effectively controlled, resulting in decrease in light transmittance at a wavelength of 550 nm and three-point bending strength of the lithium disilicate glass-ceramic finally obtained. In Example 9, the temperature for the first heat treatment is increased during the preparation, which is not conducive to the control of the crystal size of lithium disilicate, thus leading to decrease in light transmittance at a wavelength of 550 nm and three-point bending strength of the obtained lithium disilicate glass-ceramic likewise.

The lithium disilicate crystals prepared in Comparative Example 1 have a relatively low length-diameter ratio, which results in failure to form a microstructure with three-dimensional interweaving and crystal grain interlock-ing, such that the light transmittance at a wavelength of 550 nm of the lithium disilicate glass-ceramic obtained is rela-tively low, and the three-point bending strength is severely reduced.

It may be seen from the examples and comparative example as described above that in the lithium disilicate glass-ceramic according to the present disclosure, by means of increasing the size of the lithium disilicate crystals, a microstructure with three-dimensional interweaving and crystal grain interlocking may be well formed on the one hand, such that the lithium disilicate glass-ceramic has a three-point bending strength maintained between 450 and 750 MPa and a fracture toughness higher than 3.5 MPa·m^{1/2}; the increase in size of the crystals may weaken the scattering effect of the grain boundaries on light on the other hand, such that the light transmittance of a sample with a thickness of 1 mm at 550 nm is adjustable within a range of 10%-80%. The lithium disilicate glass-ceramic truly combines the excellent properties of high strength, high transparency and high fracture toughness, effectively reducing the risk of chipping and simulating the toughness and light transpar-ency of natural teeth well. The size of crystals is adjusted by optimizing the formulation composition and controlling the conditions during the heat treatment. The preparation method has a simple technological process, high economic benefit and desirable industrial application prospect.

The applicant declares that although the products and the detailed methods of the present disclosure are illustrated through the embodiments above, the present disclosure is not limited to the products and detailed methods as men-tioned above, which means the present disclosure does not have to rely on the products and detailed methods above to be implemented. Those skilled in the art should understand that any improvement to the present disclosure, equivalent replacement of the operation in the present disclosure as well as addition of auxiliary operations and selection of specific methods all fall within the protection and disclosure scope of the present disclosure.

What is claimed is:

1. A lithium disilicate glass-ceramic, wherein a raw mate-rial composition of the lithium disilicate glass-ceramic com-prises: 63-75 wt % of $SiO_2$, 13-18 wt % of $Li_2O$, 1-6 wt % of $Al_2O_3$, 1-10 wt % of $K_2O$, 2-6 wt % of $P_2O_5$, 0-4 wt % of an additive and 0-10 wt % of a colorant;

a main crystal phase of the lithium disilicate glass-ceramic is a lithium disilicate crystal, and an impurity phase of the lithium disilicate glass-ceramic is any one or a combination of at least two selected from the group consisting of lithium metasilicate, lithium phosphate and quartz; the lithium disilicate crystal has a size larger than 700 nm and not larger than 1434 nm, and a length-diameter ratio not less than 3 and not larger than 7.1;

the colorant comprises any one or a combination of at least two selected from the group consisting of $Fe_2O_3$, $TiO_2$, CuO, $Cr_2O_3$, MnO, $SeO_2$, $In_2O_3$ and a rare earth oxide; and the rare earth oxide comprises any one or a combination of at least two selected from the group consisting of $La_2O_3$, $Nd_2O_3$, $Tb_2O_3$, and $Pr_6O_{11}$.

2. The lithium disilicate glass-ceramic according to claim 1, wherein the raw material composition of the lithium disilicate glass-ceramic comprises: 65-70 wt % of $SiO_2$, 14-16 wt % of $Li_2O$, 2-5 wt % of $Al_2O_3$, 2-8 wt % of $K_2O$, 3-5 wt % of $P_2O_5$, 1-3 wt % of the additive and 2-5 wt % of the colorant.

3. The lithium disilicate glass-ceramic according to claim 1, wherein the raw material composition of the lithium disilicate glass-ceramic further comprises any one or a combination of at least two selected from the group consisting of: 0 wt %<CaO≤6 wt %, 0 wt %<BaO≤5 wt %, 0 wt %<$B_2O_3$≤10 wt %, and 0 wt %<$ZrO_2$≤10 wt % or 0 wt %<$HfO_2$≤10 wt %.

4. The lithium disilicate glass-ceramic according to claim 1, wherein the additive comprises a mixture of a monovalent metal oxide and a divalent metal oxide;

the monovalent metal oxide comprises any one or a combination of at least two selected from the group consisting of $Na_2O$, $Rb_2O$ and $Cs_2O$; and the divalent metal oxide comprises any one or a combination of at least two selected from the group consisting of MgO, SrO and ZnO.

5. The lithium disilicate glass-ceramic according to claim 1, wherein the lithium disilicate crystal is fusiform; and the lithium disilicate crystal has a microstructure with three-dimensional interweaving and crystal grain interlocking.

6. The lithium disilicate glass-ceramic according to claim 1, wherein a light transmittance of a sample of the lithium disilicate glass-ceramic with a thickness of 1 mm at 550 nm is within a range of 10%-40%, provided that the lithium disilicate crystal has a size larger than 700 nm and smaller than 1200 nm and a length-diameter ratio within a range of 3-5.

7. The lithium disilicate glass-ceramic according to claim 1, wherein a light transmittance of a sample of the lithium disilicate glass-ceramic with a thickness of 1 mm at 550 nm is within a range of 40%-80%, provided that the lithium disilicate crystal has a size not smaller than 1200 nm and not larger than 1434 nm and a length-diameter ratio not less than 5 and not larger than 7.1.

8. A method for preparing the lithium disilicate glass-ceramic according to claim 1, comprising:

(1) mixing raw materials of the lithium disilicate glass-ceramic in proportion, followed by melting to obtain a basic glass liquid; and (2) subjecting the basic glass liquid obtained in step (1) to a molding annealing treatment and a heat treatment in sequence to obtain the lithium disilicate glass-ceramic.

9. The method according to claim 8, wherein in step (1), the mixing is performed on a mixer; and in step (1), the mixing is performed for 30-300 min.

10. The method according to claim 8, wherein in step (1), the melting is performed at a temperature within a range of 1300-1600° C.; and in step (1), the melting is performed for 1-10 h.

11. The method according to claim 8, wherein in step (2), the molding annealing treatment comprises: pouring the basic glass liquid into a mold for annealing to obtain a substrate glass;

the mold is preheated to a temperature within a range of 200-500° C.;

the annealing is performed for 0.1-24 h; and after the molding annealing treatment, the treated substrate glass is cooled to room temperature.

12. The method according to claim 8, wherein the heat treatment comprises at least a first heat treatment and a last heat treatment; the first heat treatment is performed at a temperature within a range of 500-600° C.; the first heat treatment is performed for 60-240 min; the last heat treatment is performed at a temperature within a range of 800-860° C.; and the last heat treatment is performed for 1-30 min.

13. The method according to claim 12, wherein the heat treatment further comprises an intermediate heat treatment; the intermediate heat treatment is performed at a temperature within a range of 600-700° C.; and the intermediate heat treatment is performed for 30-240 min.

14. The method according to claim 12, wherein the substrate glass or an intermediate product before the last heat treatment is subjected to CAD/CAM machining to be formed into the shape of a tooth to be repaired.

15. The method according to claim 12, wherein the substrate glass or an intermediate product before the last heat treatment is formed into the shape of a tooth to be repaired by a hot pressing process or a lost wax process.

16. A method for using the lithium disilicate glass-ceramic according to claim 1, wherein the lithium disilicate glass-ceramic is used for making an oral restoration.

17. The method according to claim 16, wherein the oral restoration comprises any one of dental veneers, inlays, onlays, abutment teeth, single crowns, anterior multi-unit pontic and posterior multi-unit pontic.

18. The lithium disilicate glass-ceramic according to claim 3, wherein the raw material composition of the lithium disilicate glass-ceramic comprises: 65-70 wt % of $SiO_2$, 14-16 wt % of $Li_2O$, 2-5 wt % of $Al_2O_3$, 2-8 wt % of $K_2O$, 3-5 wt % of $P_2O_5$, 1-3 wt % of the additive and 2-5 wt % of the colorant.

19. The lithium disilicate glass-ceramic according to claim 5, wherein the raw material composition of the lithium disilicate glass-ceramic comprises: 65-70 wt % of $SiO_2$, 14-16 wt % of $Li_2O$, 2-5 wt % of $Al_2O_3$, 2-8 wt % of $K_2O$, 3-5 wt % of $P_2O_5$, 1-3 wt % of the additive and 2-5 wt % of the colorant.

* * * * *